United States Patent
Leen et al.

(10) Patent No.: US 12,050,155 B2
(45) Date of Patent: Jul. 30, 2024

(54) METHOD FOR ESTIMATING FLUX USING HANDHELD GAS SENSORS AND AN INERTIAL MEASUREMENT UNIT

(71) Applicant: ABB Schweiz AG, Baden (CH)

(72) Inventors: John B. Leen, Sunnyvale, CA (US); Joseph E. Thomaz, Santa Clara, CA (US); Douglas S. Baer, Menlo Park, CA (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 17/685,522

(22) Filed: Mar. 3, 2022

(65) Prior Publication Data

US 2023/0280230 A1    Sep. 7, 2023

(51) Int. Cl.
*G01M 3/04* (2006.01)
*F17D 5/00* (2006.01)
(Continued)

(52) U.S. Cl.
CPC .............. *G01M 3/04* (2013.01); *F17D 5/005* (2013.01); *F17D 5/02* (2013.01); *G01C 19/00* (2013.01); *G01C 21/16* (2013.01); *G01C 21/165* (2013.01); *G01M 3/26* (2013.01); *G01N 33/0009* (2013.01); *G01P 5/02* (2013.01); *G01P 15/08* (2013.01); *G01P 15/18* (2013.01)

(58) Field of Classification Search
CPC ............ G01M 3/04; G01M 3/22; G01M 3/40; G01M 3/18; G01M 3/38; G01M 3/26; G01M 3/20; G01N 33/075; G01N 21/53; G01N 21/16; G01N 33/0009; F17D 5/005; F17D 5/02; G01C 21/16; G01C 21/165; G01P 5/02
See application file for complete search history.

(56) References Cited

U.S. PATENT DOCUMENTS 5,889,199 A * 3/1999 Wong ................. G01N 21/3504
73/40
6,532,801 B1 * 3/2003 Shan ....................... G01M 3/22
73/170.04
(Continued)

FOREIGN PATENT DOCUMENTS

JP    2019-002793    *    1/2019

OTHER PUBLICATIONS

English Translation of JP2019-002793.*
(Continued)

*Primary Examiner* — Helen C Kwok
(74) *Attorney, Agent, or Firm* — Leydig, Voit & Mayer, Ltd.

(57) ABSTRACT

A system, method, and apparatus are provided for estimating a flux of fugitive gas emissions. The method is performed using a gas analyzer coupled to a sampling wand, where gas enters the inlet tip of the sampling wand prior to being sampled by the gas analyzer. The sampling wand is fixed to a mobile device that includes an inertial measurement unit. Location information from the inertial measurement unit is used to compile a high resolution geo-spatial map of gas concentration levels across a cross-sectional area of a gas plume. A near-field Gaussian plume inversion calculation is then performed to estimate the flux based on the gas concentration data and the location information.

19 Claims, 7 Drawing Sheets

(51) Int. Cl.
*F17D 5/02* (2006.01)
*G01C 19/00* (2013.01)
*G01C 21/16* (2006.01)
*G01M 3/26* (2006.01)
*G01N 33/00* (2006.01)
*G01P 5/02* (2006.01)
*G01P 15/08* (2006.01)
*G01P 15/18* (2013.01)

(56) References Cited

U.S. PATENT DOCUMENTS

| | | | | |
|---|---|---|---|---|
| 8,468,874 B2* | 6/2013 | Komninos | | G01J 5/0265 |
| | | | | 73/40 |
| 9,823,231 B1* | 11/2017 | Steele | | G01M 3/38 |
| 10,386,258 B1* | 8/2019 | Steele | | G01M 3/22 |
| 10,962,437 B1* | 3/2021 | Nottrott | | G01N 21/3504 |
| 2012/0191349 A1* | 7/2012 | Lenz | | G01N 33/0075 |
| | | | | 702/2 |
| 2015/0347647 A1* | 12/2015 | Osborne | | B09C 1/002 |
| | | | | 703/6 |
| 2016/0091476 A1* | 3/2016 | Fischer | | G01N 33/0036 |
| | | | | 73/31.02 |
| 2016/0146696 A1* | 5/2016 | Steele | | G01M 3/04 |
| | | | | 702/51 |
| 2016/0161456 A1* | 6/2016 | Risk | | G01P 5/06 |
| | | | | 702/24 |
| 2016/0307468 A1* | 10/2016 | Trumbull | | G09B 5/02 |
| 2017/0045416 A1* | 2/2017 | Hansen | | G01M 3/40 |
| 2017/0097274 A1* | 4/2017 | Thorpe | | G01C 15/00 |
| 2019/0265123 A1* | 8/2019 | Rieker | | G01N 33/0062 |
| 2020/0355573 A1* | 11/2020 | MacMullin | | G01M 3/38 |
| 2021/0055451 A1* | 2/2021 | Leen | | G01N 1/24 |
| 2021/0156793 A1* | 5/2021 | Leen | | G01S 19/01 |
| 2022/0308568 A1* | 9/2022 | Oh | | G05B 23/0221 |
| 2022/0357231 A1* | 11/2022 | Nahata | | G01M 3/16 |

OTHER PUBLICATIONS

Conley et al., "Methane emissions from the 2015 Aliso Canyon blowout in Los Angeles, CA," *Science*, 351(6279): 1317-1320 (Mar. 18, 2016).

Shah et al., "A Near-Field Gaussian Plume Inversion Flux Quantification Method, Applied to Unmanned Aerial Vehicle Sampling," *Atmosphere*, 10(7): 396 (Jul. 15, 2019).

Vaughn et al., "Comparing facility-level methane emission rate estimates at natural gas gathering and boosting stations," *Elementa: Science of the Anthropocene*, 5 (2017).

* cited by examiner

METHOD FOR ESTIMATING FLUX USING HANDHELD GAS SENSORS AND AN INERTIAL MEASUREMENT UNIT

FIELD

The present disclosure relates to a method and apparatus for mapping fugitive gas emissions to estimate flux of a gas leak. More particularly, the present disclosure relates to a method and apparatus utilizing a hand-held gas sampling wand in combination with a mobile device that includes an inertial measurement unit (IMU) to facilitate the generation of an accurate three-dimensional map of measured gas concentrations.

BACKGROUND

There is no direct manner to measure a flux of a gas leak; it must be calculated by combining measurements of air flow and gas concentration. Most typically, flux of a gas leak is measured through a process in which a tent is set up such that air flow into and out of the tent is rigorously monitored while gas concentrations into and out of the enclosure are measured. When the flow rates are combined with gas readings a flux can be established. This process requires significant setup and may not be easy to implement in any environment. Additionally, as this method can only cover discrete units of area at any one given time, this severely limits the speed at which data can be acquired.

The dimensions of the tent itself also influence the sensitivity of the flux measurement. Smaller tents offer a more precise measurement, but larger tents may better represent the region of interest. Site selection also plays a significant role. For example, a tent aligned perfectly on a crop line may yield different results than a tent that is staggered.

When implementing the tenting method, many factors exist that can affect the measurement. Significant care must be taken so as to prevent pressure buildup while maintaining a good seal around the edges of the tent in order to control the air flow in and out of the tent. Also, highly reflective materials as well as insulation may be used within the tent to limit temperature changes of the gases inside.

Alternative methods have been developed for measuring the flux of large gas leak sources by sampling gas concentrations down wind, recording the sample location using a Global Navigation and Satellite System (GNSS) tracking, and then inverting the measurements using various models to estimate the flux. While this works well when measurements are collected tens of meters downwind of the source such that the GNSS tracking accuracy can sufficiently characterize the sampling points, it fails for small sources when the measurements must be collected within a few meters of the source (i.e., due to quick dilution of the leaking gases) because the GNSS tracking accuracy cannot create an accurate map. For example, a Global Positioning System (GPS) signal may only be accurate to between 5-15 meters. If all measurements outside of 15 meters of the source are unable to detect even trace amounts of the source gas, then there is no way to plot a map of gas concentrations within 15 meters of the source using accurate location data based on the GPS signal.

A flux of gases in their native environments are inherently challenging to measure as they require not only a highly accurate gas concentration measurement over a given area, but also the capability of tracking air flow in some manner.

These is a need to solve these issues and/or other issues related to estimating gas flux using simple, non-intrusive methods.

SUMMARY

A system, method, and apparatus are provided for estimating a flux of fugitive gas emissions. The method is performed using a gas analyzer coupled to a sampling wand, where gas enters the inlet tip of the sampling wand prior to being sampled by the gas analyzer. The sampling wand is fixed to a mobile device that includes an inertial measurement unit. Location information from the inertial measurement unit is used to compile a high resolution geo-spatial map of gas concentration levels across a cross-sectional area of a gas plume. A near field Gaussian plume inversion calculation is then performed to estimate the flux based on the gas concentration data and the location information.

In accordance with a first aspect of the present disclosure, a method for estimating gas flux is provided. The method includes: determining an initial position corresponding to a source of a gas leak; collecting a plurality of samples of gas concentration measurements using a gas analyzer and a sampling wand; collecting location information along the path using an inertial measurement unit (IMU) included in a mobile device; correlating each gas concentration measurement sample with a corresponding location along the path based on the location information; and calculating an estimated flux for the gas leak based on the plurality of samples of gas concentration measurements and corresponding locations. Each sample of the gas concentration measurements is collected along a path at least in part transverse to a line from the initial position along a wind direction and located at least a minimum threshold distance from the initial position. The sampling wand is fixed relative to the mobile device.

In accordance with some embodiments of the first aspect, determining the initial position comprises prompting a user, on a display device of the mobile device, to move to a source of the gas leak and provide input indicating the mobile device is at the initial position.

In accordance with some embodiments of the first aspect, the IMU comprises at least one of a multi-axis accelerometer or a multi-axis gyroscope.

In accordance with some embodiments of the first aspect, the mobile device is one of a mobile phone or a tablet computer.

In accordance with some embodiments of the first aspect, collecting the plurality of samples of gas concentration measurements comprises moving the sampling wand along the path. A starting location of the path and an ending location of the path correspond to a minimal or undetectable concentration of a target gas in ambient air. At least one location between the starting location and the ending location corresponds to a maximum concentration level of the target gas along the path.

In accordance with some embodiments of the first aspect, the path is a horizontal line from a first side of a gas plume to a second side of the gas plume.

In accordance with some embodiments of the first aspect, the path is a two-dimensional curtain that varies in height relative to the ground as well as the transverse direction.

In accordance with some embodiments of the first aspect, correlating each gas concentration measurement sample with the corresponding location along the path based on the location information comprises: identifying a time offset associated with gas entering the sampling wand to a time when the gas analyzer takes a measurement of the gas; and matching samples of the gas concentration measurements with location information based on the time offset.

In accordance with some embodiments of the first aspect, the method further includes: collecting wind information from an anemometer communicatively coupled to the gas analyzer. The wind information is utilized by the gas analyzer to correct one or more gas concentration measurement samples or the wind information is transmitted to the mobile device and used to calculate the estimated flux.

In accordance with some embodiments of the first aspect, calculating the estimated flux comprises performing a near-field Gaussian plume inversion calculation.

In accordance with a second aspect of the present disclosure, a system is provided for estimating gas flux. The system includes: a gas analyzer; and a sampling wand coupled to the gas analyzer. The sampling wand is configured to facilitate a measurement of concentration of one or more gases collected at a tip of the sampling wand. At least one of the gas analyzer or the sampling wand includes an interface that is communicatively coupled to a corresponding interface of a mobile device. The mobile device includes at least one processor and an inertial measurement unit (IMU). The at least one processor is configured to: determine an initial position corresponding to a source of a gas leak; receive a plurality of samples of gas concentration measurements via the interface; collect location information along the path using the IMU; correlate each gas concentration measurement sample with a corresponding location along the path based on the location information; and calculate an estimated flux for the gas leak based on the plurality of samples of gas concentration measurements and corresponding locations. Each sample of the gas concentration measurements is collected along a path at least in part transverse to a line from the initial position along a wind direction and located at least a minimum threshold distance from the initial position. The sampling wand is fixed relative to the mobile device.

In accordance with some embodiments of the second aspect, determining the initial position comprises prompting a user, on a display device of the mobile device, to move to a source of the gas leak and provide input indicating the mobile device is at the initial position.

In accordance with some embodiments of the second aspect, the IMU comprises at least one of a multi-axis accelerometer or a multi-axis gyroscope.

In accordance with some embodiments of the second aspect, the mobile device is one of a mobile phone or a tablet computer.

In accordance with some embodiments of the second aspect, collecting the plurality of samples of gas concentration measurements comprises moving the sampling wand along the path. A starting location of the path and an ending location of the path correspond to a minimal or undetectable concentration of a target gas in ambient air, and at least one location between the starting location and the ending location corresponds to a maximum concentration level of the target gas along the path.

In accordance with some embodiments of the second aspect, the path is a two-dimensional curtain that varies in height relative to the ground as well as the transverse direction.

In accordance with some embodiments of the second aspect, calculating the estimated flux comprises performing a near-field Gaussian plume inversion calculation.

In accordance with a third aspect of the present disclosure, a mobile device is provided that includes at least one processor and an inertial measurement unit (IMU). The at least one processor is configured to: determine an initial position corresponding to a source of a gas leak; receive a plurality of samples of gas concentration measurements via an interface communicatively coupled to at least one of a gas analyzer or a sampling wand; collect location information along the path using the IMU; correlate each gas concentration measurement sample with a corresponding location along the path based on the location information; and calculate an estimated flux for the gas leak based on the plurality of samples of gas concentration measurements and corresponding locations. The sampling wand is fixed relative to the mobile device. Each sample of the gas concentration measurements is collected along a path at least in part transverse to a line from the initial position along a wind direction and located at least a minimum threshold distance from the initial position.

In accordance with some embodiments of the third aspect, determining the initial position comprises prompting a user, on a display device of the mobile device, to move to a source of the gas leak and provide input indicating the mobile device is at the initial position.

In accordance with some embodiments of the third aspect, calculating the estimated flux comprises performing a near-field Gaussian plume inversion calculation.

DETAILED DESCRIPTION

Figure 1:
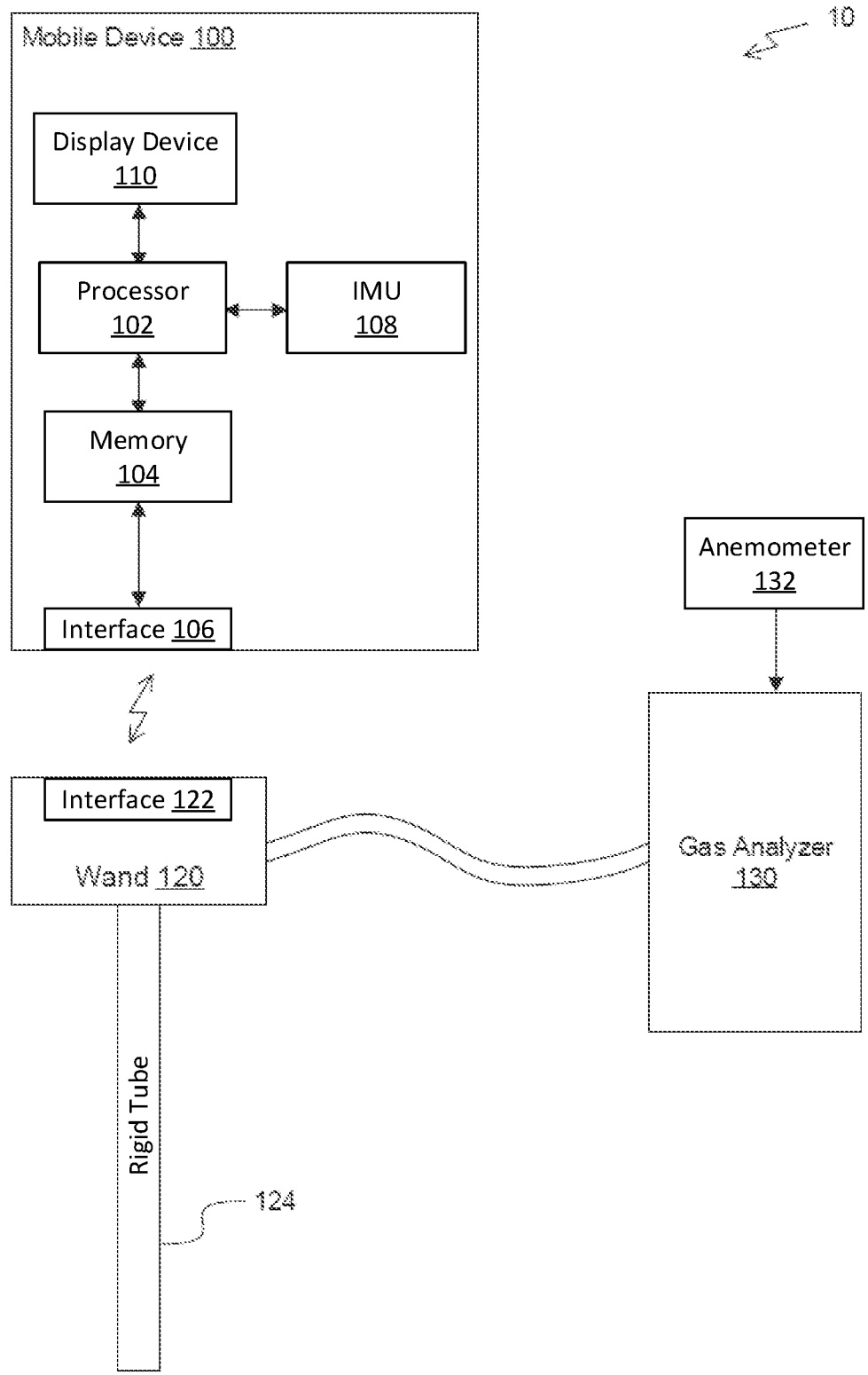
FIG. 1 illustrates a system for measuring concentration levels of gases in an environment, in accordance with an embodiment of the present disclosure.

Measuring flux of gases in an environment can be performed with a handheld flux analyzer comprising a sampling wand coupled to a laser-based trace gas analyzer in order to measure concentration levels of one or more gases simultaneously. The types of gases detectable include gases such as methane, ethane, propane, and/or added odorants. In some embodiments, multiple types of gases can be detected at the same time.

The following disclosure describes a technique for estimating the flux of fugitive gas emissions. The technique involves measuring, via a gas analyzer attached to a sampling wand, gas concentration levels over an area that intersects a gas plume from a gas leak. The use of a sampling wand, separate and distinct from the gas analyzer, allows for a high degree of spatial resolution to be achieved when the location of the inlet tip of the sampling wand is tracked using an inertial measurement unit. In one embodiment, the inertial measurement unit is provided as part of a mobile device such as a mobile phone or tablet computer, which is paired with the sampling wand and fixed relative thereto during the collection of gas concentration measurements. Thus use of accelerometers, gyroscopes, and/or magnetometers implemented by an inertial measurement unit facilitates determining the exact position of the inlet tip of the sampling wand with a high degree of accuracy, especially when compared against other techniques that rely on GPS signals or other less accurate location information. In some embodiments, GPS location information can be augmented by the location information from the inertial measurement unit in order to provide both a coarse position due to GPS and a fine positioning from the inertial measurement unit relative to the coarse position. Because the inlet tip of the sampling wand is fixed relative to the mobile device, an exact position of the inlet tip can be calculated using a linear transformation based on the location information of the mobile device. This location information can then be correlated with the gas concentration measurement data collected using the gas analyzer to create a geo-spatial map of gas concentration levels associated with a gas plume.

One benefit of this technique is that the distance between the source and the measurement can be automatically measured by the inertial measurement unit when the user begins the process by placing the inlet tip of the sampling wand at the location where the source of the gas leak is identified. Determining an accurate distance between the source of the gas leak and the measurement can greatly reduce the uncertainties in the flux calculation, and measuring the distance automatically based on location information from the inertial measurement unit can reduce error introduced by a user that manually enters a value for this distance. A dilution factor used in the calculation of the flux is critically dependent on the distance to the source of the gas leak.

Using the distance to the source of the gas leak and a high-resolution geo-spatial map of gas concentration measurements, a flux estimation operation is performed utilizing a near field Gaussian plume inversion method.

FIG. 1 illustrates a system 10 for measuring concentration levels of gases in an environment, in accordance with an embodiment of the present disclosure. The system 10 includes a mobile device 100, a sampling wand 120, and a gas analyzer 130. In an embodiment, the sampling wand 120 includes an interface 122 to connect to the mobile device 100 and a rigid tube 124 that provides a means for sampling gases at an inlet tip of the rigid tube located at a distal end from the body of the sampling wand 120. Ambient air enters the inlet tip and is directed to the gas analyzer 130 via a tube connecting the sampling wand 120 to the gas analyzer 130.

In an embodiment, the mobile device 100 is a handheld device, such as a mobile phone or tablet computer, that includes at least one processor 102, a memory 104, an interface 106, an inertial measurement unit (IMU) 108, and a display device 110. In one embodiment, the interface 106 may be a wired interface and may comprise a female port configured to accept a male connector of the interface 122 of the sampling wand 120. In another embodiment, the interface 106 may be a wireless interface such as a Bluetooth interface, Wireless Fidelity (Wi-Fi) interface, or other Near Field Communication (NFC) interface. In the case of a wireless interface, both the mobile device 100 and the sampling wand 120 may include a transceiver as well as one or more antennas for transmitting and/or receiving wireless signals.

In an embodiment, the gas analyzer 130 is constantly analyzing the ambient air entering the inlet tip of the rigid tube 124 of the sampling wand 120 to determine a concentration of the gas by using, e.g., integrated cavity output spectroscopy (ICOS). In other embodiments, the gas analyzer 130 may detect the concentration of the gas using other known techniques such as cavity ringdown spectroscopy (CRDS), Harriot cells, White cells, cavity enhanced absorption spectroscopy, mid-infrared laser-based absorption spectroscopy, tunable diode laser spectroscopy, or any sensor functioning as a high-precision gas analyzer that is sensitive to, e.g., 10 parts-per-billion (ppb) concentrations of methane or other types of gas. In an embodiment, the gas analyzer 130 may be disposed in a backpack or otherwise included in a harness that can be worn or carried by a user.

The mobile device 110 may include one or more applications in the memory 104 that, when executed by a processor 102, cause the mobile device to measure a concentration of gases in the atmosphere and create a map of gas concentrations in an area proximate a source of a gas leak. The mobile device 110 may use location information sampled from the IMU 108 in order to correlate gas concentration measurements with a location of the sampling wand 120 at a time of taking the measurement. Because the IMU 108 provides much more accurate location information than, for example, a GNSS signal, the accuracy of estimates of flux for even small gas leaks may be improved.

In an embodiment, the sampling wand 120 is rigidly connected to the mobile device 100. For example, in the case of a wired connection between interface 106 and interface 122, the connection of the male connector with a female port may be sufficient to fix the sampling wand 120 relative to the mobile device 100 such that the location of the mobile device 100, as measured by the IMU 108, may be used to determine the location of the sampling wand 120, given a known offset between the mobile device 100 and the inlet tip of the rigid tube 124. It will be appreciated that the offset may be known at the time of manufacture of the sampling wand 120 and/or may be manually entered by a user of the mobile device 100 based on a configuration or type of the sampling wand 120.

However, in other embodiments where the interface 106 and interface 122 are a wireless interface, then the sampling wand 120 may be attached to the mobile device 100 by any other technically feasible means. For example, the sampling wand 120 can include a member that comprises a case that attaches to or otherwise surrounds at least part of the mobile device 100. As an alternative, in some embodiments, the sampling wand 120 can include a clip, clamp, suction cup, or the like, which may be used to temporarily affix the sampling wand 120 to the mobile device 100. In some embodiments, a case of the mobile device 100 or the chassis of the mobile device 100 includes means for securing the sampling wand 120. For example, a case for the mobile device 100 can be designed to include a clip that is configured to accept and securely hold the rigid tube of the sampling wand 120 on the side of the mobile device 100. As an alternative to the clip, the sampling wand 120 may include magnets that, when brought proximate corresponding magnets in the case, secure the sampling wand 120 to the case.

As the sampling wand 120 and mobile device 100 are separate and distinct components, the sampling wand 120 should be fixed relative to the mobile device 100 such that the IMU 108 of the mobile device 100 can be used to locate the inlet tip of the sampling wand 120. While it is possible to perform the technique discussed below without fixing the sampling wand 120 to the mobile device 100, care would need to be taken when taking measurements to manually specify the offset location of the inlet tip from the mobile device and keep the offset location constant during measurement collection. If the offset location varies during measurements, then the accuracy of the flux estimation may decrease. Thus, it is strongly preferred to attach the sampling wand 120 to the mobile device 100 while taking measurements.

It will be appreciated that there is a delay from the gas entering the inlet tip of the sampling wand 120 until that gas enters the gas analyzer 130. In an embodiment, location information sampled by the IMU 108 is associated with a time delay such that a measurement at time t is correlated with location information collected at time t−d, where d represents the time delay. The time delay is affected by a length of the sampling wand 120, a length of tubing connecting the sampling wand 120 to the gas analyzer 130, a diameter of the sampling wand 120 and/or the tubing, and a flow rate of the gas through the gas analyzer 130. It will be appreciated that the samples of location information and samples of gas concentration and/or other measurement data (e.g., wind speed and/or direction, temperature, pressure, etc.) may be collected independently and then correlated at a later point in time using the associated time delay to match up samples of the two or more series of data collected at different points in time.

In some embodiments, the gas analyzer 130 may be connected to an optional anemometer 132 configured to measure wind speed and/or direction. In an embodiment, the anemometer 132 is a sonic anemometer that provides real-time wind speed and direction information to the gas analyzer 130. The anemometer 132 may communicate with the gas analyzer 130 via a wired or wireless interface. In some embodiments, the gas analyzer 130 uses wind speed and/or direction information from the anemometer to adjust the measurement information collected for a sample.

Although not shown explicitly in FIG. 1, the sampling wand 120 and the gas analyzer 130 may communicate directly via either a wired or wireless interface. For example, the tubing between the sampling wand 120 and the gas analyzer 130 may be incorporated into an assembly that includes a wired interface for communication between the sampling wand 120 and the gas analyzer 130. Thus, the measurement information, which may include both gas concentration level information as well as wind speed and/or direction from the anemometer 132, may be communicated from the gas analyzer 130 to the sampling wand 120, which can then transmit the measurement information to the mobile device 100 via the interface 122.

Alternatively, in other embodiments, the sampling wand 120 may not include the interface 122 but communicates directly with the gas analyzer 130 via the aforementioned wired or wireless interface. The gas analyzer 130 is then configured to communicate wirelessly with the mobile device 100. For example, the gas analyzer 130 may include a transceiver and one or more antennas that enable the gas analyzer to communicate with the mobile device 100 over a Wi-Fi connection or via Bluetooth. While the sampling wand 120 is fixed or otherwise attached to the mobile device, the sampling wand 120 does not communicate any information to the mobile device 100 as all measurement information is collected by the mobile device 100 directly from a wireless interface of the gas analyzer 130.

Figure 2:
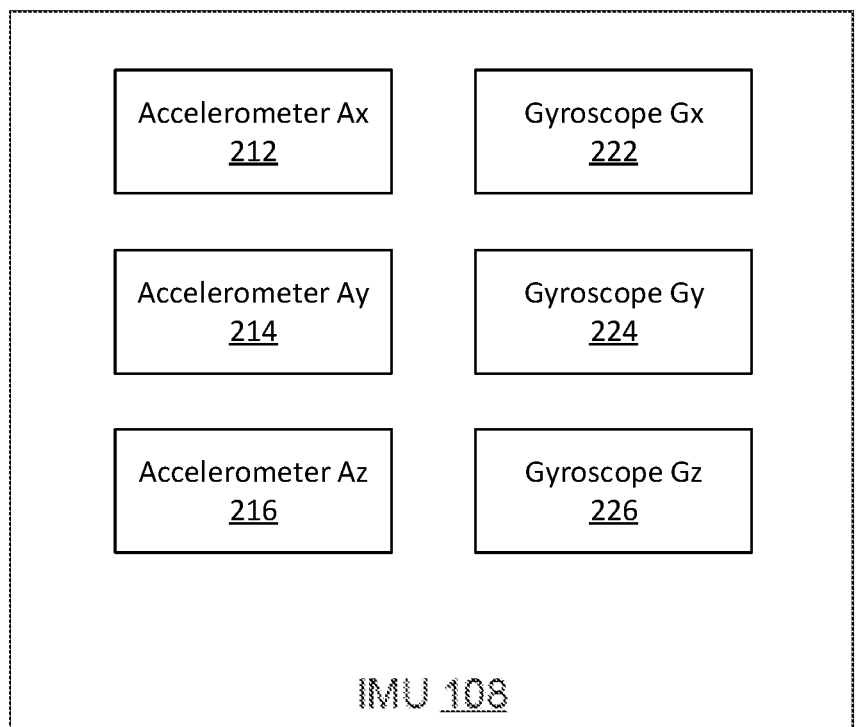
FIG. 2 illustrates the inertial measurement unit (IMU) of the mobile device, in accordance with an embodiment of the present disclosure.

FIG. 2 illustrates the inertial measurement unit (IMU) 108 of the mobile device 100, in accordance with an embodiment of the present disclosure. As depicted in FIG. 2, the IMU 108 may include at least one accelerometer configured to measure translation of the mobile device 100 for one or more axes (e.g., an x-axis, a y-axis, and a z-axis). The IMU 108 may also include at least one gyroscope configured to measure rotation of the mobile device 100 around one or more axes. In an embodiment, the IMU 108 includes a first accelerometer 212 for measuring a translation along an x-axis, a second accelerometer 214 for measuring a translation along a y-axis, and a third accelerometer 216 for measuring a translation along a z-axis. The IMU 108 also includes a first gyroscope 222 for measuring a rotation around the x-axis, a second gyroscope 224 for measuring a rotation around the y-axis, and a third gyroscope 226 for measuring a rotation around the z-axis. In some embodiments, the rotations may be referred to as roll, pitch, and yaw. In some embodiments, other sensors such as magnetometers, micro-electrical mechanical systems (MEMS) devices, or the like may be included in lieu of or in addition to the accelerometers and gyroscopes. Furthermore, although the accelerometers and/or gyroscopes are depicted as separate units, in some embodiments, the sensors can be combined in a single, multi-axis sensor.

It will be appreciated that the IMU 108 measures relative translational and/or rotational accelerations, which can be used to determine a relative translation and/or rotation of the mobile device 100. In one embodiment, the location information generated by the IMU 108 is used by the mobile device 100 to track a position and/or orientation of the mobile device 100 relative to an initial position. As will be discussed in more detail below, the initial position can be specified manually by a user and may, in at least one instance, be specified as indicating a source of a gas leak. The location information, therefore, may specify a location of the mobile device 100 relative to a source of the gas leak.

Figure 3:
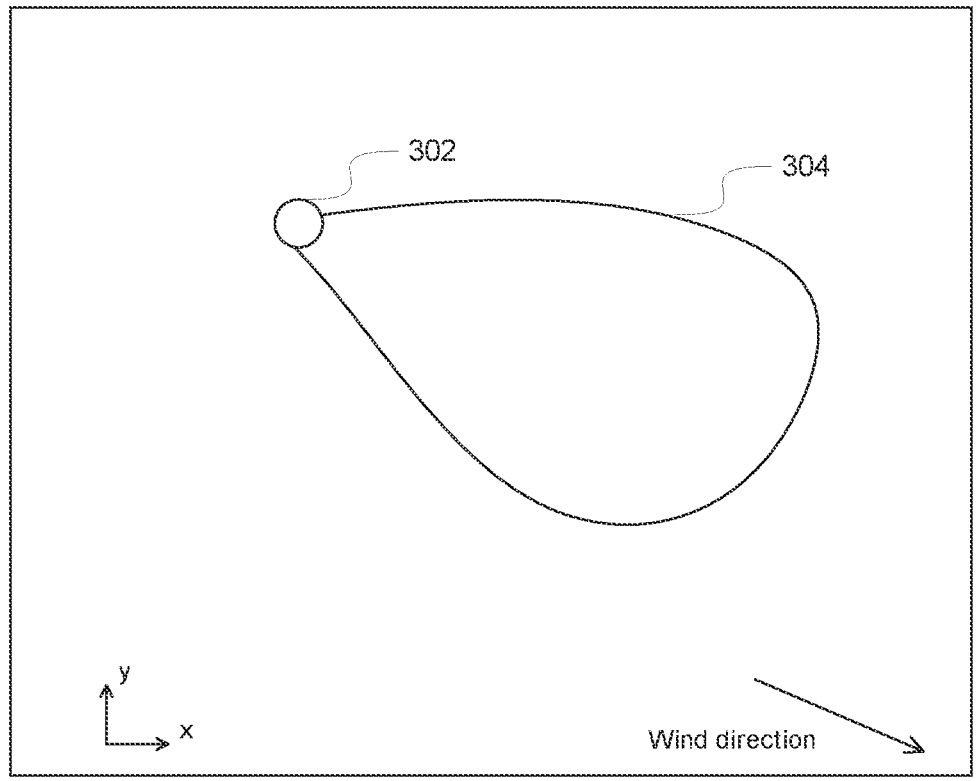
FIG. 3 is a plan view of a gas leak showing a plume of fugitive gas emanating from a source of the gas leak, in accordance with an embodiment of the present disclosure.

FIG. 3 is a plan view of a gas leak showing a plume of fugitive gas emanating from a source of the gas leak, in accordance with an embodiment of the present disclosure. As depicted in FIG. 3, a gas leak has a source 302 located at a specific location in the environment. In some cases, such as a ruptured pipe, it may be easy to discover the source of the gas leak. In other cases, where gas is leaking from underground, for example, it may be more difficult to decipher the source of the gas leak. Various techniques for locating a primary source of a gas leak are known by those of skill in the art, including IMU assisted guidance and/or bio-mimetic leak investigation methods. One such technique is detailed in U.S. Patent Application No. 2021/0156793, titled "SYSTEMS AND METHODS FOR LOCATING SOURCES OF FUGITIVE GAS EMISSIONS", filed on Nov. 22, 2019, which is hereby incorporated by reference in its entirety.

A gas plume 304 is shown emanating from the source 302. As will be understood by those of skill in the art, gas being emitted from a source 302 will disperse in the ambient air surrounding the leak and will flow downwind based on prevailing wind direction and speed. Depending on the specific type of gas, the gas may also rise or sink based on the relative density of the gas and the density of the ambient air. The outline of the plume 304 indicates an area where the gas concentration level of a target gas emanating from the source 302 is above a threshold level. Although FIG. 3 only shows the plume 304 in a top-down plan view, it will be appreciated that the plume is actually a three-dimensional volume.

Figure 4:
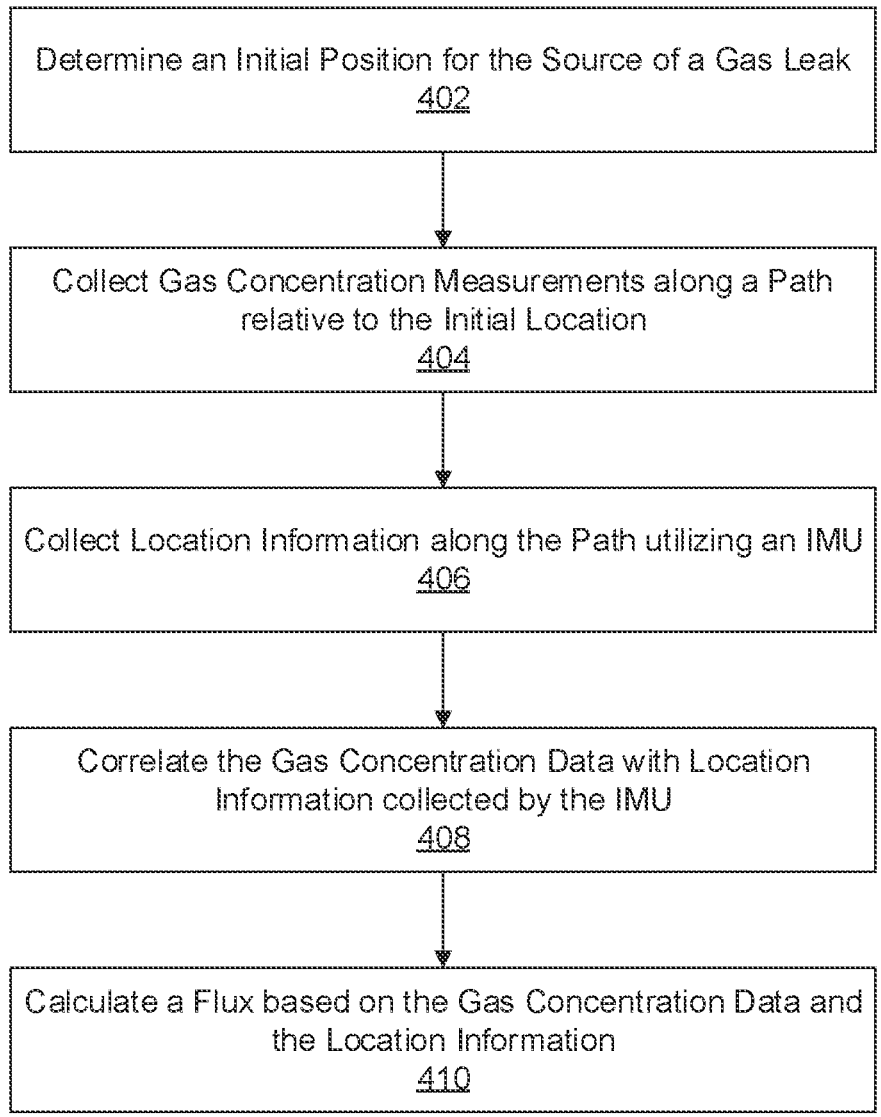
FIG. 4 is a flow diagram of a method for estimating flux of a gas leak, in accordance with an embodiment of the present disclosure.

FIG. 4 is a flow diagram of a method for estimating gas flux, in accordance with some embodiments of the present disclosure. The method 400 can be performed, at least in part, by the system 10 of FIG. 1. For example, the mobile device 100 can receive gas concentration measurements from the sampling wand 120 and combine the gas concentration measurements with location information collected from sampling the IMU 108 of the mobile device 100.

At step 402, an initial position corresponding to a source of a gas leak is determined. In an embodiment, an application may be executed on the mobile device 100, and the application may include a user interface shown on a display device 110 of the mobile device 100. To begin a gas flux estimation operation, a user is prompted by the user interface on the mobile device 100 to move the sampling wand 120 proximate a source of the gas leak. In some embodiments, the gas analyzer may take gas concentration measurements and direct the user to move in a direction of increasing gas concentration by displaying an indication on the display device 110 indicating a possible location of the source of the gas leak.

Once the user is proximate the source of the gas leak, the user may provide input via the user interface to set the current location of the mobile device 100 as the initial position. In one embodiment, the user presses a button on the mobile device 100 or a user interface element displayed on the mobile device 100 to indicate to the application that the mobile device 100 is located at the initial position. In some embodiments, the user may also enter an offset distance and/or direction that indicates a relative location of the mobile device 100 to the source of the gas leak. For example, if it is not safe to place the mobile device 100 near the source of the gas leak, then the user could specify that the gas leak is, e.g., 3 meters in front of the mobile device at the time of setting the initial position.

It will be appreciated that while the initial position is identified prior to collection of the gas concentration measurements, in other embodiments, the initial position can be identified during or after collection of the gas concentration measurements but before calculation of the estimated flux.

In some embodiments, the user can identify multiple source locations as a set of initial positions. For example, a gas leak from underground may have two or more locations where the gas is escaping the ground that may be separately identified at step 402. Alternatively, the user can specify an area that encloses one or more of the sources of the gas leak by tracing the area using the inlet tip of the sampling wand 120.

At step 404, a plurality of samples of gas concentration measurements are collected using a gas analyzer 130 and a sampling wand 120. In an embodiment, the user is prompted by the user interface to walk a minimum threshold distance from the source of the gas leak in a direction predominantly downwind of the gas leak. For example, the user could be directed to walk 5 meters downwind from the source of the gas leak. The user is then prompted to walk along a path that is at least in part transverse to a line from the initial position along a wind direction and located at least a minimum threshold distance from the initial position. Preferably, the path should include a starting location on one side of the gas plume and an ending location on another side of the gas plume such that gas concentration levels at both the starting location and ending location are minimal or undetectable and the path passes through the gas plume.

In an embodiment, the user is directed to walk transverse to the gas plume while the gas analyzer 130 monitors a gas concentration level. Once the gas concentration level is below a minimum threshold (or undetectable), then user is prompted by the mobile device 100 to begin collecting gas concentration measurements along the path by walking through the gas plume in the opposite direction substantially transverse to the wind direction. The gas analyzer 130 may be configured to collect samples of gas concentrations periodically at a particular sampling frequency.

In one embodiment, the path is a one-dimensional path and the sampling wand 120 is held at a constant height relative to the ground level (e.g., the path consists of a line horizontal to the ground). In another embodiment, the path is a two-dimensional curtain and the sampling wand 120 is held at different heights relative to the ground either during a single pass of the path (i.e., moving the sampling wand 120 up and down as the user slowly traverses the path) or held at different heights during multiple passes of the path, each pass the sampling wand 120 being held at a different height (e.g., 1 foot, 3 feet, or 5 feet above ground level). The two-dimensional curtain creates a raster scan of a cross-section of the gas plume with concentration levels sampled at different horizontal and vertical positions along the path.

In yet other embodiments, the path is a three-dimensional path where the sampling wand 120 is moved in both horizontal directions and vertical directions along a substantially transverse path, but also additional passes are taken at different distances from the source of the gas leak such that gas concentration measurement samples are collected at different points in a sample volume of the gas plume.

At step 406, location information is collected along the path using an inertial measurement unit (IMU) included in a mobile device. Occurring substantially simultaneously with collecting the gas concentration measurement samples, a location of the mobile device 100 is also tracked based on location information collected from the IMU 108. In an embodiment, location information from the IMU 108 is collected and used to track a location of the mobile device 100 relative to the source of the gas leak (i.e., the initial position).

In some embodiment, the location information from the IMU can be augmented with location information from a GPS signal or some other low accuracy GNSS signal. The GPS signal can provide a course indication of location for a measurement, while the location information from the IMU can provide the important high resolution spatial information important to increase the accuracy of the flux estimation.

At step 408, each gas concentration measurement sample is correlated with a corresponding location along the path based on the location information. In an embodiment, the samples of the location information create a time-series of samples that is correlated with the time-series of gas concentration measurement samples. In other words, each gas concentration measurement sample is matched with a corresponding location sample, based on a time offset. Again, as there is a delay in the gas entering the inlet tip of the sampling wand 120 until the gas enters the gas analyzer 130 and a sample is collected, the samples of the location of the sampling wand 120 correspond to a delayed sample generated by the gas analyzer 130.

In an embodiment, the time delay is preset based on the dimensions of the sampling wand 120 and/or tubing connecting the sampling wand 120 to the gas analyzer 130. For example, the time delay can be stored in a memory included in the sampling wand 120 and communicated to the mobile device 100 via the interface 122. In another embodiment, the mobile device 100 can prompt the user to manually enter a time delay associated with the sampling wand 120 connected to the gas analyzer 130.

At step 410, an estimated flux for the gas leak is calculated based on the plurality of samples of gas concentration measurements and corresponding locations. In an embodiment, a near field Gaussian plume inversion method may be used to calculate the estimated flux. In addition to the gas concentration measurements and corresponding locations, this technique may also require background gas concentration (i.e., a gas concentration value upwind of the source of the gas leak), wind direction and/or speed measurements collected by the anemometer 132, and an atmospheric gas mass density value. This technique calculates a measured flux density, which is compared to a two-dimensional Gaussian with known height and center used as a model for the gas plume. The 2D Gaussian is subsequently distorted using a crosswind mixing factor and a vertical mixing factor to accurately model the shape of the plume. When fitting the distorted 2D Gaussian to the measured flux density, the scaling factor contains an estimate of the flux implicitly. This method is described in more detail in Shah et al., "A Near-Field Gaussian Plume Inversion Flux Quantification Method, Applied to Unmanned Aerial Vehicle Sampling," Atmosphere, Jul. 15, 2019, the entire contents of which are herein incorporated by reference.

The fit of the distorted 2D Gaussian relies on two floating parameters: the flux and the vertical mixing factor. In an embodiment, these parameters are extracted by minimizing the sum of the squared residuals of all the modelled 2D Gaussian and measured flux densities. A least squared error or similar function may be used during the minimization.

In other embodiments, other techniques for calculating the estimated flux may be implemented. These techniques may include, but are not limited to, scaled-average gas maxima, trained regression models, mass-balance calculations, and Bayesian accumulation and estimation.

In an embodiment, the method 400 further includes measuring a gas concentration upwind of the source of the gas leak. The gas concentration measured upwind can provide a background gas concentration unrelated to the source of the gas leak. In addition, additional measurements can be collected, such as wind speed and/or direction at multiple locations using two or more anemometers which may be separate and distinct from the anemometer 132 attached to the gas analyzer 130. In some embodiments, the wind speed and/or direction information can be entered manually via a user interface of the mobile device 100 rather than communicated from the anemometer 132 to the gas analyzer 130.

Figure 5:
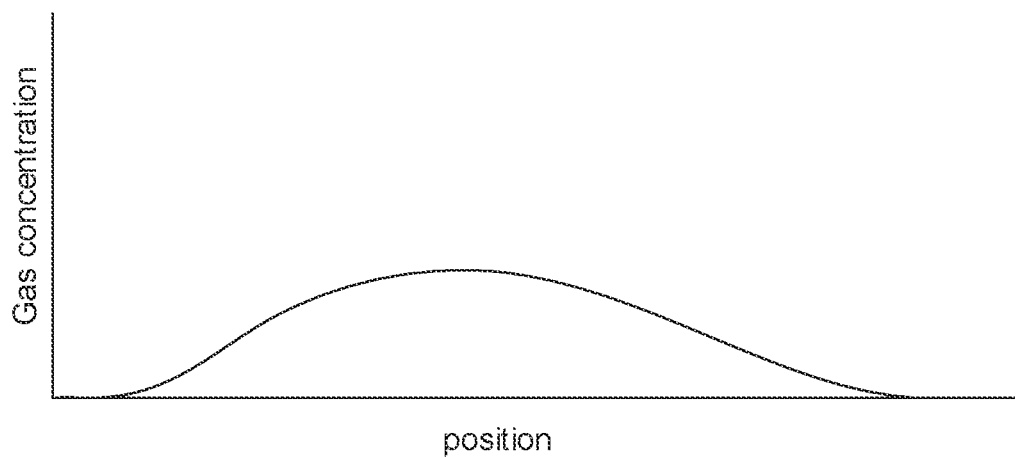
FIG. 5 is a conceptual illustration of the map of gas concentration collected by the mobile device, in accordance with an embodiment of the present disclosure

FIG. 5 is a conceptual illustration of the map of gas concentration collected by the mobile device 100, in accordance with an embodiment of the present disclosure. The map is a simple line graph that shows increasing gas concentration levels as the sampling wand 120 is moved from the starting location towards the ending location along the path. At a point near the middle of the path, the gas concentration level reaches a maximum and then begins to decrease as the sampling wand 120 is moved towards the ending location.

It will be appreciated that the line graph may represent a plurality of discrete samples and not a continuous measurement, with each sample corresponding to a location along the path. It will also be appreciated that the locations along the path are represented by a single axis, which may correspond to a linear path at a constant height above ground level. In other embodiments, the map may be a three-dimensional graph that shows gas concentrations in an x-z plane, where x represents a direction substantially perpendicular to the wind direction and z represents a height above the ground level, and each <x, z> location in the plane is associated with a gas concentration value. In yet other embodiments, the map may comprise volumetric data that associates each <x, y, z> location with a gas concentration value.

Figure 6:
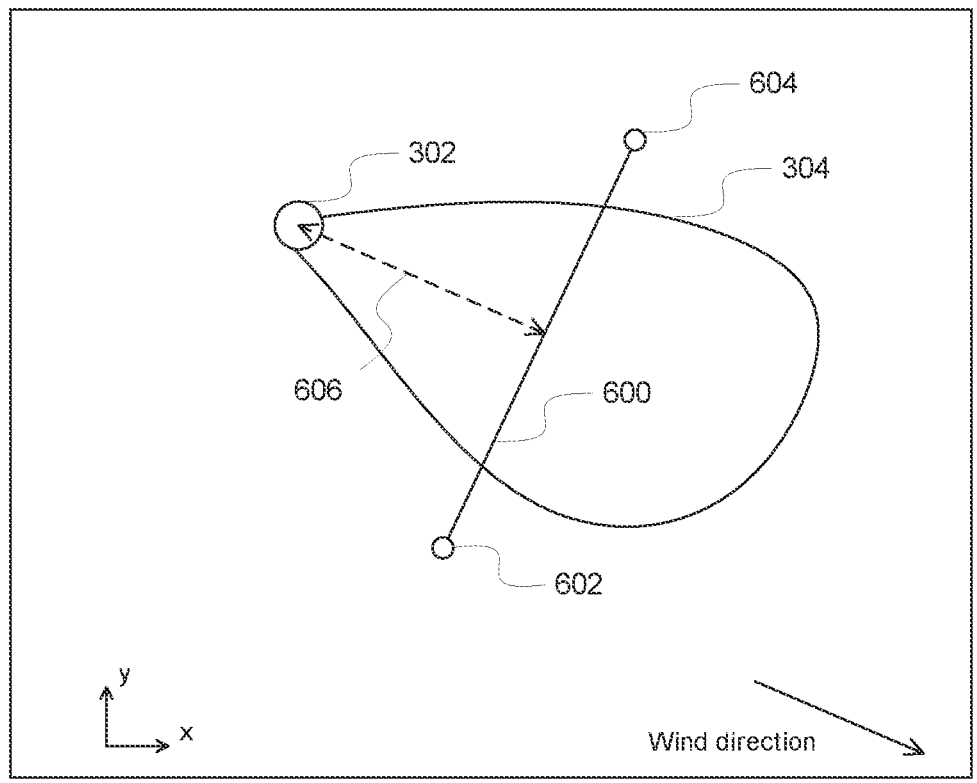
FIG. 6 is a conceptual illustration of the approximate location of a path for sampling gas concentration levels relative to the gas plume of FIG. 3, in accordance with an embodiment of the present disclosure.

FIG. 6 is a conceptual illustration of the approximate location of a path 600 for sampling gas concentration levels relative to the gas plume 304 of FIG. 3, in accordance with an embodiment of the present disclosure. Once the user has located the source 302 of the gas leak, the user is prompted to move a threshold distance 606 from the source 302 in a direction of the prevailing wind (i.e., downwind of the gas leak). Moving substantially transverse to the wind direction, the user then moves to the starting location 602. In an embodiment, the user may continue walking perpendicular to the wind direction until the gas concentration level falls below a minimum level in order to identify the starting location 602. Once at the starting location, the user then begins collecting gas concentration measurement data by moving along the path 600 in the direction of the ending location 604.

It will be appreciated that the path 600 is shown in a top-down plan view, and may represent a straight line from the starting location 602 to the ending location 604 at a constant height in the z direction. In certain embodiments, however, the path 600 may represent a serpentine path in the x-z plane such that the gas concentration measurements are taken over a curtain that represents a certain area of a cross-section of the gas plume.

In yet other embodiments, gas concentration measurements can be collected corresponding to multiple paths 600 at different threshold distances 606 from the source in order to sample the volume of the gas plume in three dimensions rather than only taking a sample at a specific cross-section of the gas plume.

Figure 7A:
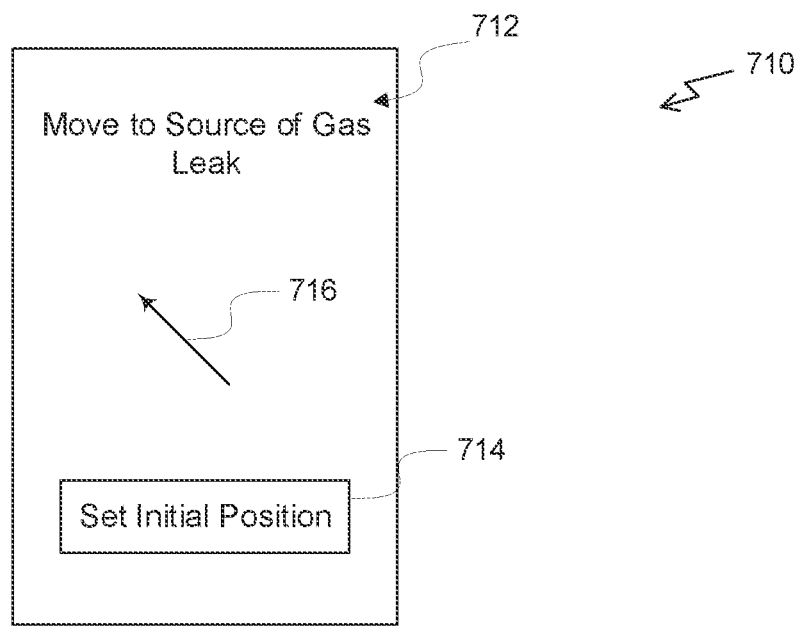
FIGS. 7A & 7B is a view of a user interface implemented by the mobile device, in accordance with an embodiment of the present disclosure.
Figure 7B:
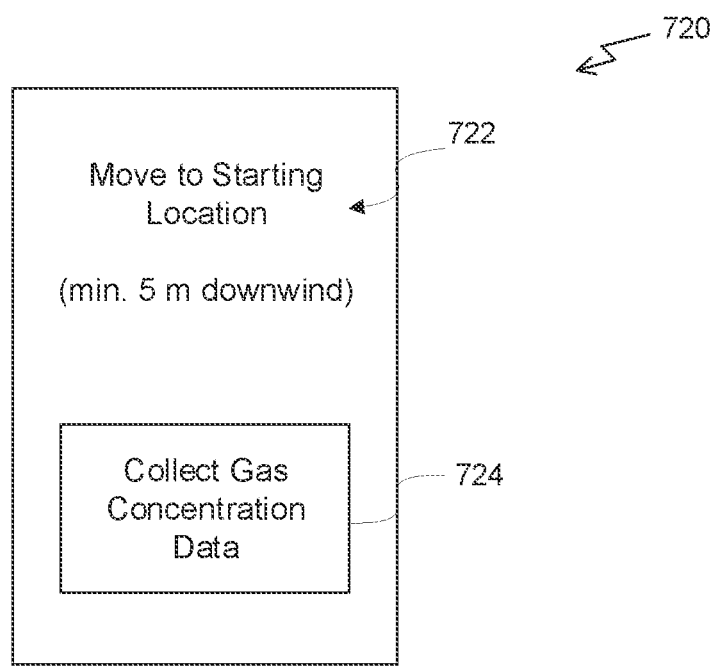

FIGS. 7A & 7B is a view of a user interface 710 implemented by the mobile device 100, in accordance with an embodiment of the present disclosure. The user interface 710 may be generated by one or more applications executing on the processor 102 of the mobile device 100 and displayed on the display device 110. In an embodiment, the display device 110 is a touch-sensitive display that senses touch input provided on a surface of the display device 110.

As depicted in FIG. 7A, the user interface 710 includes a prompt 712 comprising text and/or images that can provide instructions or other information to a user of the mobile device 100. The user interface 710 may also include a user interface element 714 such as a virtual button that can be selected to provide feedback from the user. In an embodiment, the user interface 710 is displayed when the user begins a flux estimation operation in order to aid the user in providing the necessary data to perform the calculation. The user is instructed to move to the source of the gas leak and select the user interface element 714 to indicate the initial position. The initial position may be set to <0, 0, 0> as a location.

In an embodiment, the user interface 710 may also include an indicator 716, such as an arrow, showing a direction of the likely source of the gas leak. It will be appreciated that the gas analyzer 130 can be used to collect continuous gas concentration level readings and ascertain a direction associated with increasing gas concentration levels. The arrow may point to the area of high gas concentration as the direction of the likely source of the gas leak. In other embodiments, any technically feasible technique for identifying the source of the gas leak can be implemented and/or incorporated into various aspects of the user interface 710. For example, As depicted in FIG. 7B, the user interface 720 includes a prompt 722 comprising text and/or images that can provide instructions or other information to the user of the mobile. In this case, the prompt instructs the user to move to the starting location for taking gas concentration measurements, which is the starting location of the path, as discussed above. The user interface 720 also includes a user interface element 724 that allows the user to provide input to start the data collection as the user walks the path to take gas concentration measurements.

It will be appreciated that the user interfaces 710 & 720 are only show as examples of the type of user interface elements that may be displayed to a user to help facilitate the collection of gas concentration measurements. It will be appreciated that additional user interface elements and/or additional user interfaces may be displayed on the mobile device in addition to or in lieu of the user interfaces described above.

It should be understood that the arrangement of components illustrated in the attached Figures are for illustrative purposes and that other arrangements are possible. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the embodiments as claimed.

What is claimed is:

1. A method for estimating gas flux, the method comprising:
   determining an initial position corresponding to a source of a gas leak;
   collecting a plurality of gas concentration measurements using a gas analyzer and a sampling wand, wherein each sample of the gas concentration measurements is collected along a path at least in part transverse to a line from the initial position along a wind direction and located at least a minimum threshold distance from the initial position;
   collecting location information along the path using an inertial measurement unit (IMU) included in a mobile device, wherein the sampling wand is fixed relative to the mobile device, wherein the IMU comprises a multi-axis gyroscope;
   correlating each of the plurality of gas concentration measurements with a corresponding location along the path based on the location information, wherein correlating each of the plurality of gas concentration measurements with the corresponding location along the path based on the location information comprises:
      identifying a time offset associated with each sample of gas entering the sampling wand to a time when the gas analyzer takes a measurement of the each sample;
      determining a first time at which the gas analyzer takes a measurement of the each sample; and
      matching the each sample with the corresponding location obtained at a second time, wherein the second time is obtained by subtracting the time offset from the first time;
   generating a geo-spatial map of gas concentration levels associated with the gas leak based on the correlations; and
   calculating, based on the geo-spatial map an estimated flux for the gas leak relative to an area corresponding to the geo-spatial map.

2. The method of claim 1, wherein determining the initial position comprises prompting a user, on a display device of the mobile device, to move to the source of the gas leak and provide input indicating the mobile device is at the initial position.

3. The method of claim 1, wherein the IMU further comprises a multi-axis accelerometer.

4. The method of claim 1, wherein collecting the plurality of gas concentration measurements comprises moving the sampling wand along the path, wherein a starting location of the path and an ending location of the path correspond to a minimum concentration of a target gas in ambient air, and wherein at least one location between the starting location and the ending location corresponds to a maximum concentration level of the target gas along the path.

5. The method of claim 4, wherein the path is a horizontal line from a first side of a gas plume to a second side of the gas plume.

6. The method of claim 4, wherein the path is a two-dimensional curtain that varies in height relative to a ground as well as the path at least in part transverse to the line.

7. The method of claim 1, further comprising collecting wind information from an anemometer communicatively coupled to the gas analyzer, wherein the wind information is utilized by the gas analyzer to correct one or more of the plurality of gas concentration measurements or the wind information is transmitted to the mobile device and used to calculate the estimated flux.

8. The method of claim 1, wherein calculating the estimated flux comprises performing a near-field Gaussian plume inversion calculation.

9. A system for estimating gas flux, the system comprising:
   a gas analyzer; and
   a sampling wand coupled to the gas analyzer and configured to facilitate a measurement of concentration of one or more gases collected at a tip of the sampling wand, wherein at least one of the gas analyzer or the sampling wand includes an interface that is communicatively coupled to a corresponding interface of a mobile device that includes at least one processor and an inertial measurement unit (IMU) comprising a multi-axis gyroscope, and wherein the at least one processor is configured to:

determine an initial position corresponding to a source of a gas leak;

receive a plurality of gas concentration measurements via the interface, wherein each sample of the gas concentration measurements is collected along a path at least in part transverse to a line from the initial position along a wind direction and located at least a minimum threshold distance from the initial position;

collect location information along the path using the IMU, wherein the sampling wand is fixed relative to the mobile device;

correlate each of the plurality of gas concentration measurements with a corresponding location along the path based on the location information, wherein to correlate each of the plurality of gas concentration measurements with the corresponding location along the path based on the location information, the processor is further configured to:

identify a time offset associated with each sample of gas entering the sampling wand to a time when the gas analyzer takes a measurement of the each sample;

determine a first time at which the gas analyzer takes a measurement of the each sample; and match the each sample with the corresponding location obtained at a second time, wherein the second time is obtained by subtracting the time offset from the first time;

generate a geo-spatial map of gas concentration levels associated with the gas leak based on the correlations; and calculate, based on the geo-spatial map, an estimated flux for the gas leak relative to an area corresponding to the geo-spatial map.

10. The system of claim 9, wherein determining the initial position comprises prompting a user, on a display device of the mobile device, to move to a source of the gas leak and provide input indicating the mobile device is at the initial position.

11. The system of claim 9, wherein the IMU further comprises a multi-axis accelerometer.

12. The system of claim 9, wherein receiving the plurality of gas concentration measurements comprises moving the sampling wand along the path, wherein a starting location of the path and an ending location of the path correspond to a minimal or undetectable concentration of a target gas in ambient air, and wherein at least one location between the starting location and the ending location corresponds to a maximum concentration level of the target gas along the path.

13. The system of claim 12, wherein the path is a two-dimensional curtain that varies in height relative to a ground as well as the path at least in part transverse to the line.

14. The system of claim 9, wherein calculating the estimated flux comprises performing a near-field Gaussian plume inversion calculation.

15. A mobile device comprising at least one processor and an inertial measurement unit (IMU), wherein the at least one processor is configured to:

determine an initial position corresponding to a source of a gas leak;

receive a plurality of gas concentration measurements via an interface communicatively coupled to at least one of a gas analyzer or a sampling wand, wherein the sampling wand is fixed relative to the mobile device, and wherein each sample of the gas concentration measurements is collected along a path at least in part transverse to a line from the initial position along a wind direction and located at least a minimum threshold distance from the initial position;

collect location information along the path using the IMU, wherein the IMU comprises a multi-axis gyroscope;

correlate each of the plurality of gas concentration measurements with a corresponding location along the path based on the location information, wherein to correlate each of the plurality of gas concentration measurements with the corresponding location along the path based on the location information, the processor is further configured to:

identify a time offset associated with each sample of gas entering the sampling wand to a time when the gas analyzer takes a measurement of the each sample;

determine a first time at which the gas analyzer takes a measurement of the each sample; and match the each sample with the corresponding location obtained at a second time, wherein the second time is obtained by subtracting the time offset from the first time;

generate a geo-spatial map of gas concentration levels associated with the gas leak based on the correlations; and calculate, based on the geo-spatial map, an estimated flux for the gas leak relative to an area corresponding to the geo-spatial map.

16. The mobile device of claim 15, wherein determining the initial position comprises prompting a user, on a display device of the mobile device, to move to the source of the gas leak and provide input indicating the mobile device is at the initial position.

17. The method of claim 1, wherein the collected plurality of gas concentration measurements are stored as a time-series of gas concentration measurements, wherein the time-series of gas concentration measurements is generated by associating the each sample of the gas concentration measurements with a corresponding time at which the each sample was collected.

18. The method of claim 17, wherein the collected location information is stored as a time-series of locations, wherein the time-series of locations is generated by associating each location in the time-series of locations with the corresponding time at which the each sample was collected.

19. The method of claim 1, wherein the time offset is based on dimensions of the sampling wand and/or tubing connecting the sampling wand to the gas analyzer and a flow rate of gas through the gas analyzer.

* * * * *